United States Patent [19]
Takamizawa et al.

[11] Patent Number: 4,461,908
[45] Date of Patent: Jul. 24, 1984

[54] METHOD FOR THE PREPARATION OF METHYL HYDROGENSILANES

[75] Inventors: Minoru Takamizawa, Tokyo; Mitsuo Umemura, Gunma; Taishi Kobayashi, Niigata, all of Japan

[73] Assignee: Shin-Etsu Chemical Co., Ltd., Tokyo, Japan

[21] Appl. No.: 481,867

[22] Filed: Apr. 4, 1983

[30] Foreign Application Priority Data

Dec. 17, 1982 [JP] Japan ............................... 57-222541

[51] Int. Cl.$^3$ .............................................. C07F 7/08
[52] U.S. Cl. ..................................... 556/430; 556/468
[58] Field of Search ................................ 556/430, 468

[56] References Cited

U.S. PATENT DOCUMENTS

| | | | |
|---|---|---|---|
| 2,513,123 | 6/1950 | Wagner | 556/468 |
| 2,598,434 | 5/1952 | Mohler et al. | 556/468 |
| 2,598,435 | 5/1952 | Mohler et al. | 556/468 |
| 4,079,071 | 3/1978 | Neale | 556/468 |

FOREIGN PATENT DOCUMENTS 2409010  8/1974  German Democratic Rep. ................................... 556/468

OTHER PUBLICATIONS

"J. Am. Chem. Soc.", 101, No. 18, pp. 5427–5428, 1979.

Primary Examiner—Paul F. Shaver
Attorney, Agent, or Firm—Toren, McGeady and Stanger

[57] ABSTRACT

The invention provides a novel and efficient method for the preparation of methyl hydrogensilanes, e.g. dimethyl silane, 1,1,2,2-tetramethyl disilane and 1,1,2,2,3,3-hexamethyl trisilane, with large demand in the industry of silicones as an intermediate for the synthesis of other valuable organosilicon compounds such as methyl hydrogenchlorosilanes. The inventive method comprises pyrolysis of a methyl polysilane composed of at least 60% by moles of dimethylsilicon units, the balance being monomethyl- and trimethylsilicon units, at a temperature in the range from 350° to 800° C.

3 Claims, No Drawings

METHOD FOR THE PREPARATION OF METHYL HYDROGENSILANES

BACKGROUND OF THE INVENTION

The present invention relates to a method for the preparation of methyl hydrogensilanes or, more particularly, for the preparation of dimethylsilane and 1,1,2,2-tetramethyl disilane by the pyrolysis of a methyl polysilane compound.

Methyl hydrogenchlorosilane compounds, e.g. dimethyl monochlorosilane, are useful in the industry of silicones as an intermediate for the synthetic preparation of various organosilicon compounds having reactive or functional groups by virtue of the reactivity of the hydrogen atoms directly bonded to the silicon atom and the hydrolyzability of the chlorine atom in the molecule into a silanolic hydroxy group susceptible to dehydration condensation to give a siloxane linkage. Notwithstanding the large demand for such methyl hydrogenchlorosilanes for the applications as mentioned above, the supply of the compounds in the silicone industry is limited. That is, methyl hydrogenchlorosilanes are obtained industrially only as a by-product is a relatively small amount in the so-called direct method for the synthesis of methyl chlorosilanes by the reaction of metallic silicon and methyl chloride. Various attempts have been made, of course, to develop an efficient method for increasing the yield of the methyl hydrogenchlorosilanes in the above mentioned direct method or for establishing another efficient synthetic route for the preparation thereof though without noticeable success to give only a few percent yield of, for example, methyl dichlorosilane $CH_3SiHCl_2$. In particular, it has been eagerly desired to establish an industrially feasible method for the preparation of dimethyl monochlorosilane $(CH_3)_2HSiCl$ since the yield of this particular methyl hydrogenchlorosilane as a byproduct in the direct method is very small even in comparison with the yield of the above mentioned methyl dichlorosilane.

It is one of possible ways to obtain the above mentioned dimethyl monochlorosilane from dimethylsilane $(CH_3)_2SiH_2$ or 1,1,2,2-tetramethyl disilane $(CH_3)_2HSi—SiH(CH_3)_2$ utilizing the reactivity of the silicon-bonded hydrogen atoms or the susceptibility of the Si—Si linkage to scission. Unfortunately, the supply of these methyl hydrogensilanes is also limited since no industrially practicable method is known for the preparation thereof.

SUMMARY OF THE INVENTION

It is therefore an object of the present invention to provide a novel and efficient method for the preparation of methyl hydrogensilanes represented by the general formula $H_mSi_n(CH_3)_{2n+2-m}$, in which n and m are each a positive integer with the proviso that $(2n+2-m)$ is a positive integer or, more particularly, dimethylsilane and 1,1,2,2-tetramethyl disilane, which may be used as an intermediate for the synthetic preparation of, for example, dimethyl monochlorosilane demanded in large quantities in the industry of silicones.

The method of the present invention for the preparation of the above mentioned methyl hydrogensilanes or for the preparation of dimethylsilane, 1,1,2,2-tetramethyl disilane and 1,1,2,2,3,3-hexamethyl trisilane expressed by the above given general formula having the integers m and n equal to 2 and 1, 2 or 3, respectively, comprises pyrolyzing a methyl polysilane, which is a compound having more than three silicon atoms per molecule as composed of methylsilicon units $CH_3Si\equiv$, dimethylsilicon units $(CH_3)_2Si=$ and trimethylsilicon units $(CH_3)_3Si—$, at a temperature in the range from 350° to 800° C. or, preferably, from 650° to 800° C. In particular, it is preferable that the starting methyl polysilane compound is composed of at least 60% by moles of the dimethylsilicon units based on the total molar amount of the above mentioned three kinds of the units of which the methyl polysilane compound is composed.

DETAILED DESCRIPTION OF THE PREFERRED EMBODIMENTS

The above mentioned inventive method for the preparation of the methyl hydrogensilanes has been completed not as a target of the experimental investigations undertaken by the inventors with the above object but on the base of an unexpected discovery made in the course of the experiments for the method of preparation of the so-called methyl carbosilane polymers having a main skeleton of recurring silicon-to-carbon linkages by the pyrolyzing polymerization of a dimethyl polysilane compound that the volatile decomposition product formed in the above mentioned pyrolyzing polymerization of the dimethyl polysilane compound is composed mainly of dimethylsilane and 1,1,2,2-tetramethyl disilane accompanied by relatively small amounts of trimethylsilane $(CH_3)_3SiH$, monomethylsilane $CH_3SiH_3$, 1,1,2,2,3,3-hexamethyl trisilane $(CH_3)_2HSi—Si(CH_3)_2—SiH(CH_3)_2$ and the like. The present invention has been completed as a result of the extensive investigations following the above discovery in order to establish the optimum conditions for the pyrolysis of the starting methyl polysilane compound as well as the optimum types thereof capable of giving the highest yield of the desired methyl hydrogensilanes.

To describe the method of the present invention in further detail, the starting material used in the method of the present invention is a methyl polysilane which is a compound obtained by the dechlorination condensation reaction of one or a mixture of methyl chlorosilanes with metallic sodium or lithium and composed of the above mentioned three kinds of the units, i.e. mono-methyl-, dimethyl- and trimethylsilicon units. Preferably, the molar content of the dimethylsilicon units relative to the total amount of the three kinds of units in the methyl polysilane compound should be as high as possible to exceed 60% by moles or, in particular, the methyl polysilane compound is a dimethyl polysilane having a cyclic or linear molecular structure as expressed by the structural formulas

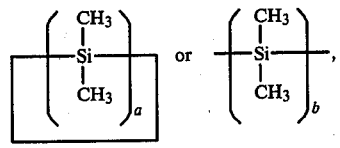

respectively, in which a is a positive integer of, for example 5 to 8 or, predominantly, 6 and b is a positive integer of, for example, up to 40 as obtained by the dechlorination condensation reaction of dimethyl dichlorosilane though not limited thereto. The linear methyl polysilane compounds are insoluble in any organic solvents but fusible at about 350° C. or higher with simultaneous decomposition more or less. Other types of the methyl polysilane compounds which may be used in the inventive method as the starting material include a dechlorination cocondensation product of a silane mixture composed of dimethyl dichlorosilane, methyl trichlorosilane and trimethyl chlorosilane as well as methyl chlorodisilane compounds of the general formula $(CH_3)_pSi_2Cl_{6-p}$, in which p is a positive integer of 1 to 4, obtained as high-boiling byproducts in the direct method for the synthesis of the methyl chloromonosilanes, with metallic sodium leading to the formation of the three kinds of the methylsilicon units. Alternatively, suitable methyl polysilane compounds can be obtained by the methylation of the remaining silicon-bonded chlorine atoms in a methyl chloropolysilane compound prepared by the pyrolyzing polymerization of the above mentioned methyl chlorodisilane compounds in the presence of a catalyst as is disclosed in Japanese Patent Publication 55-49621. At any rate, the molar content of the dimethylsilicon units should preferably be 60% or higher when higher yields of the dimethylsilane and 1,1,2,2-tetramethyl disilane are desired in the pyrolysis product of the inventive method.

The principle of the inventive method is the pyrolysis of the methyl polysilane compound so that the desired methyl hydrogensilanes can be obtained by merely introducing the starting material into a reaction zone of a reactor filled with packings such as Raschig rings and kept at a temperature in the range from 350° to 800° C. although the results of the pyrolysis reaction differ widely depending on the temperature at which the reaction of pyrolysis is performed. For example, pyrolysis of the methyl polysilane compound at a temperature of 350° to 600° C. is accompanied more or less by the formation of a methyl polycarbosilane polymer having a main skeleton of recurring silicon-to-carbon linkages along with the thermal decomposition of the starting material. On the other hand, higher yields of the methyl hydrogensilanes can be obtained by increasing the temperature of pyrolysis over 600° C. though with the formation of small amounts of inorganic materials such as silicon carbide or elementary silicon. When the temperature of pyrolysis is higher than 800° C., the thermal decomposition of the methyl groups in the starting material is so violent that the yield of the inorganic materials, i.e. silicon carbide and elementary silicon, is rapidly increased resulting in the decrease in the yields of the desired dimethylsilane, 1,1,2,2-tetramethyl disilane and other methyl hydrogensilane compounds. This is the reason for the above mentioned limitation in the temperature for carrying out the pyrolysis of the methyl polysilane compounds.

The methyl polysilane compound as the starting material used in the inventive method is obtained in a powdery, resinous or oily form according to the degree of polymerization and molecular configuration. Any methyl polysilanes are suitable as the starting material regardless of the above mentioned forms provided that the methyl polysilane can be molten at an elevated temperature. When the methyl polysilane has a linear molecular configuration with a relatively large degree of polymerization, however, it is preferable that the pyrolysis thereof is conducted in steps rather than directly subjecting the starting material to the pyrolysis in one step at a temperature of 600° to 800° C. For example, the first step of the stepwise pyrolysis is continuous introduction of the starting methyl polysilane in the form of a liquid or solid melting at 200° C. or higher into a reaction column filled with suitable packings, e.g. Raschig rings, and kept at a temperature of 350° to 500° C. at a relatively large rate of feeding, i.e. to have a relatively short reaction time, to be converted into liquid oligomeric methyl polysilanes having a relatively low molecular weight with eventual formation of vaporizable methyl hydrogensilanes. Then the pyrolysis of the oligomeric methyl polysilanes is conducted either batchwise in a reaction vessel with agitation at 400° to 600° C. under an inert atmosphere taking a relatively long reaction time to be converted into methyl hydrogensilanes with simultaneous formation of methyl carbosilane polymers or as a continuous process by introducing the oligomer into a reactor column kept at 600° to 800° C. to pyrolyze it completely within a relatively short reaction time into methyl hydrogensilanes without formation of methyl carbosilane polymers.

As is mentioned before, the methyl hydrogensilane product obtained according to the method of the invention is mainly composed of dimethylsilane and 1,1,2,2-tetramethyl disilane along with a relatively small amount of 1,1,2,2,3,3,-hexamethyl trisilane which can be purified by rectifying distillation of the crude reaction product. These methyl hydrogensilanes are themselves useful as an intermediate for the synthesis of various kinds of organosilicon compounds by utilizing the reactivity of the hydrogen atoms directly bonded to the silicon atoms in the molecule along with the silicon-bonded methyl groups. It is, however, the most important use of these methyl hydrogensilanes that they are converted to methyl hydrogenchlorosilanes by the reaction with chlorine, hydrogen chloride or various kinds of organochlorosilanes followed by the hydrolysis of the methyl hydrogenchlorosilanes to produce methyl hydrogenopolysiloxane having silicon-bonded hydrogen atoms useful in the technology of silicones. For example, dimethyl monochlorosilane $(CH_3)_2HSiCl$ is obtained by the reaction of dimethylsilane with hydrogen chloride or dimethyl dichlorosilane or by the reaction of 1,1,2,2-tetramethyl disilane with chlorine and very useful as a reactant to introduce a dimethyl hydrogensilyl group at a chain end of polysiloxane linkages. Further, the reaction of this dimethyl monochlorosilane with acetylene gives vinyl dimethyl chlorosilane of the formula $(CH_2=CH-)(CH_3)_2SiCl$, which is a useful compound as a reactant to introduce a vinyl dimethyl silyl group at a chain end of polysiloxane linkages. When the above mentioned trisilane is not desired as a product, this trisilane may be further subjected to the pyrolysis reaction to be converted into more useful dimethylsilane and tetramethyl disilane.

Following are examples to illustrate the method of the present invention in further detail.

EXAMPLE 1

A steel-made reactor column having an inner diameter of 42 mm and filled up to the top level of the undermentioned heating zone with Raschig rings of fused quartz glass was held upright and heated at 440° C. in a furnace having a heating zone of 200 mm length. A powder of dimethyl polysilane, which had been prepared by the dechlorination polycondensation reaction of dimethyl dichlorosilane with metallic sodium in xylene, was introduced into the reactor at the column top by use of a screw feeder at a rate of 0.217 g/hour.ml of the unfilled column volume as carried by a gentle downstream of nitrogen gas to be pyrolyzed in the column. The products by the pyrolysis reaction were discharged out of the column bottom and collected by chilling. There were obtained an oligomeric liquid product in a yield of 84.7% by weight and a gaseous product mainly composed of dimethylsilane boiling at about −20° C. in a yield of 15.1% by weight.

In the next place, the above obtained oligomer was introduced into a steel-made reactor column of 1.5 mm inner diameter held in an inclined disposition and kept at 720° C. in a tubular furnace having a heating zone of 800 mm length at a feed rate of 0.045 g/hour.ml of the column volume by use of a metering pump to effect the pyrolysis thereof. The product was gaseous and collected as a liquid condensate in a trap chilled in a bath of dry ice-methanol to give a yield of 86% by weight based on the feed. The balance of the yield was a powdery inorganic material of light yellow color. Rectifying distillation of the above obtained liquid condensate indicated that it was composed of a trace amount of methylsilane $CH_3SiH_3$, 51.0% by weight of dimethylsilane, 7.0% by weight of trimethylsilane $(CH_3)_3SiH$, 20.0% by weight of 1,1,2,2-tetramethyl disilane and 17.8% by weight of high-boiling fractions including 1,1,2,2,3,3-hexamethyl trisilane.

In a similar manner to the above procedure for the pyrolysis of the oligomer, the mixture of the high-boiling fractions including the hexamethyl trisilane was subjected to further pyrolysis by introducing into the reactor column kept at 680° C. to give 86.7% by weight of a volatile material composed of 65.0% by weight of dimethylsilane, 7.5% by weight of trimethylsilane, 6.4% by weight of 1,1,2,2-tetramethyl disilane and 7.8% by weight of the unreacted hexamethyl trisilane, the balance being mostly an inorganic solid material.

EXAMPLE 2

A reactor column of 45 mm inner diameter and 1000 mm length made of fused quartz glass and having two rolled sheets of mesh screens of stainless steel inserted into the central portion thereof was held upright and heated at a constant temperature of 650° C. in a vertical-type tubular furnace having a heating zone of 200 mm length and a powder of dimethyl polysilane was continuously introduced into this reactor at the top thereof at a feed rate of 0.15 g/hour.ml of the column volume by use of a screw feeder to effect the pyrolysis reaction.

The gaseous product produced by the pyrolysis was collected over 5 hours, during which feeding of 240 g of the methyl polysilane was completed, by condensation in a trap chilled in a bath of dry ice-methanol. The amount of the condensate liquid was 217 g as composed of 55% by weight of dimethylsilane, 8% by weight of trimethylsilane and 12% by weight of 1,1,2,2-tetramethyl disilane, the balance of 24% of high-boiling matters including 1,1,2,2,3,3-hexamethyl trisilane and a powdery solid.

EXAMPLE 3

Into a flask made of fused quartz glass and equipped with a stirrer were introduced 500 g of a powder of dimethyl polysilane, which had been prepared by the dechlorination polycondensation reaction of dimethyl dichlorosilane with metallic sodium, and heated to slowly increase the temperature under a gentle stream of nitrogen gas. When the temperature had reached a temperature of about 350° C., beginning of the formation of a gaseous product was noticed as a result of the polymerization of the dimethyl polysilane with thermal decomposition as was evidenced by the vciscosity increase of the reaction mixture in the flask.

After 10 hours of gradual temperature increase up to 450° C., the reaction mixture in the flask was kept at this temperature for 3 hours, during which the volatilized product formed by the pyrolysis reaction was collected in a trap chilled in a bath of dry ice-methanol as a liquid condensate. This liquid condensate, obtained in a yield of 270 g, was composed of 55.0% by weight of dimethylsilane, 4.2% by weight of trimethylsilane, 22.3% by weight of 1,1,2,2-tetramethyl disilane, 14.6% by weight of 1,1,2,2,3,3-hexamethyl trisilane and 3.9% by weight of higher-boiling materials.

After distilling off all of the above mentioned vola-ile products, there were left 211 g of a resinous material in the quartz flask having a softening point of 70° to 75° C. This solid material had an average molecular weight of about 800 and was identified by the infrared spectral analysis to be a polycarbosilane having $-Si-CH_2-Si-$ linkages and silicon-bonded hydrogen atoms.

EXAMPLES 4 TO 7

Substantially the same experimental procedure was undertaken in each of the Examples as in Example 2 except that the methyl polysilane compound as the feed material had been prepared from a mixture of dimethyl dichlorosilane, methyl trichlorosilane and trimethyl chlorosilane by the dechlorination reaction with metallic sodium and the temperature of the reactor column was kept at 680° C. instead of 650° C. The composition of the silane mixture as the feed and the composition of the pyrolysis products were as shown in Table 1 below. As is understood from the results, the yields of the desired pyrolysis products decreased when the molar content of the dimethylsilicon units in the starting silane mixture was 60% or smaller with somewhat increased yield of the high-boiling pyrolysis products as well as deposition of inorganic materials such as silicon carbide on the inner walls of the reactor column.

EXAMPLE 8

An approximately equimolar disilane mixture composed of dimethyl tetrachlorodisilane and trimethyl trichlorodisilane as obtained from the high-boiling by-product formed in the direct synthesis method of methyl chlorosilanes from methyl chloride and metallic silicon was heated in the presence of hexamethyl phosphoroamide as a catalyst and polymerized by the pyrolyzing polycondensation with simultaneous removal of the methyl chlorosilanes by distillation to be converted into a methyl chloropolysilane.

TABLE 1

| | | Example No. | | | |
|---|---|---|---|---|---|
| | | 4 | 5 | 6 | 7 |
| Composition of methyl polysilane feed, % by moles | $(CH_3)_2Si=$ units | 80 | 65 | 90 | 55 |
| | $CH_3Si\diagup\diagdown$ units | 15 | 20 | 5 | 30 |
| | $(CH_3)_3Si-$ units | 5 | 15 | 5 | 15 |
| Yield of product | Total feed, grams | 250 | 250 | 250 | 250 |
| | grams | 210 | 180 | 220 | 105 |
| | % by weight | 84.0 | 72.0 | 88.0 | 42.0 |
| Composition of product, % by | Dimethyl silane | 50.5 | 45.3 | 53.2 | 35.6 |
| | Methyl silane | 2.8 | 5.2 | 2.3 | 7.6 |
| | Trimethyl silane | 4.6 | 7.0 | 7.2 | 7.5 |
| | 1,1,2,2-Tetra- | 15.3 | 12.1 | 13.5 | 10.2 |

TABLE 1-continued

| | | Example No. | | | |
|---|---|---|---|---|---|
| | | 4 | 5 | 6 | 7 |
| weight | methyl disilane Trisilane and higher-boiling matter | 26.8 | 30.4 | 23.8 | 39.1 |

Methylation of this chlorine-containing polysilane with methyl Grignard reagent CH$_3$MgCl gave a methyl polysilane composed of 72% by moles of dimethylsilicon units, 8% by moles of methylsilicon units and 20% by moles of trimethylsilicon units and having a viscosity of 476 centistokes and an average molecular weight of about 850.

Into a quartz glass-made were taken 500 g of the above prepared methyl polysilane which was heated with agitation under a gentle stream of nitrogen gas to note that the pyroslysis reaction began when the temperature had reached 340° C. The temperature was further increased taking 15 hours up to 470° C. where the reaction mixture was kept for additional one hour.

As a result of the above described pyrolysis reaction of the methyl polysilane, 270 g of volatile materials were obtained as composed of 52.0% of dimethylsilane, 6.5% of trimethyl silane, 1.2% of methyl silane, 24.3% of 1,1,2,2-tetramethyl disilane, 10.1% of 1,1,2,2,3,3-hexamethyl trisilane and 5.9% of other higher-boiling materials. The residue left in the quartz glass-made flask after the evaporation of the above mentioned volatile products was a resinous solid in an amount of 217 g having a softening temperature of 135° to 142° C. and the infrred spectral analysis thereof indicated that it was a methyl carbosilane polymer having —Si—CH$_2$—Si— linkages and silicon-bonded hydrogen atoms.

EXAMPLE 9

The same methyl polysilane compound as used in Example 8 was introduced into the same reactor column as used in Example 2 heated at 630° C. in a vertical-type tubular furnace continuously at the top thereof at a feed rate of 1 g/minute over a period of 4 hours to be pyrolyzed therein and to give 221 g of the pyrolysis products corresponding to 92.0% of the starting material and composed of 58.5% of dimethyl silane, 6.5% of trimethyl silane, 0.8% of methyl silane, 20.3% of 1,1,2,2-tetramethyl disilane, 9.2% of 1,1,2,2,3,3-hexamethyl trisilane and 4.7% of other higher-boiling materials. It was noted that the inner walls of the reactor column were very little stained by the deposition of the inorganic pyrolysis products after completrion of the above procedure of pyrolysis.

What is claimed is:

1. A method for the preparation of a methyl hydrogensilane represented by the general formula H$_m$Si$_n$(CH$_3$)$_{2n+2-m}$, in which n is a positive integer of 1, 2 or 3 and m is a positive integer with the proviso that (2n+2−m) is a positive integer, which comprises pyrolyzing a methyl polysilane having more than three silicon atoms per molecule and composed of methylsilicon units CH$_3$Si≡, dimethylsilicon units (CH$_3$)$_2$Si= and trimethylsilicon units (CH$_3$)$_3$Si—, of which at least 60% of the total molar content of the said three kinds of the units are the dimethylsilicon units, at a temperature in the range from 350° to 800° C.

2. The method for the preparation of the methyl hydrogensilane as claimed in claim 1 wherein the pyrolysis of the methyl polysilane is performed in two steps composed of a first step of pyrolyzing the methyl polysilane at a temperature in the range from 350° to 600° C. to form an oligomeric liquid and a second step of pyrolyzing the thus obtained oligomeric liquid at a temperature in the range from 600° to 800° C.

3. The method for the preparation of the methyl hydrogensilane as claimed in claim 1 wherein the methyl polysilane is a dimethyl polysilane compound having a cyclic or linear molecular structure.

* * * * *